United States Patent
Beaver et al.

(10) Patent No.: US 12,351,555 B2
(45) Date of Patent: Jul. 8, 2025

(54) PROCESS FOR SYNTHESIZING APREMILAST

(71) Applicant: AMGEN INC., Thousand Oaks, CA (US)

(72) Inventors: Matthew G. Beaver, Natick, MA (US); Carolyn Cohen, Somerville, MA (US); Neil Fred Langille, Thousand Oaks, CA (US); Simone Spada, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 17/728,575

(22) Filed: Apr. 25, 2022

(65) Prior Publication Data

US 2022/0348542 A1    Nov. 3, 2022

Related U.S. Application Data

(60) Provisional application No. 63/179,632, filed on Apr. 26, 2021.

(51) Int. Cl.
*C07D 209/48*    (2006.01)

(52) U.S. Cl.
CPC ........ *C07D 209/48* (2013.01); *C07B 2200/13* (2013.01)

(58) Field of Classification Search
CPC .................................................. C07D 209/48
See application file for complete search history.

(56) References Cited

FOREIGN PATENT DOCUMENTS

| CN | 105085373 A | 11/2015 |
|---|---|---|
| CN | 107698485 A | 2/2018 |
| CN | 111039846 A | 4/2020 |
| IN | 201621013195 | 10/2017 |
| WO | 2009/120167 A1 | 10/2009 |
| WO | 2016/199031 A1 | 12/2016 |
| WO | WO 2016/192694 A1 * | 12/2016 |
| WO | 2017/033116 A1 | 3/2017 |
| WO | 2017/039537 A1 | 3/2017 |
| WO | 2017/059040 A1 | 4/2017 |
| WO | 2018/203192 A1 | 11/2018 |
| WO | 2019/021303 A1 | 1/2019 |

OTHER PUBLICATIONS

Battilocchio, et al. (Battilocchio et al., "Flow Chemistry" captured via webarchive.org on Sep. 21, 2019 <https://web.archive.org/web/20180420125656/http://www.organic-chemistry.org/topics/flowchemistry.shtm> (Year: 2019).*

Diab et al., "Technoeconomic Evaluation of Multiple Mixed Suspension-Mixed Product Removal (MSMPR) Crystallizer Configurations for Continuous Cyclosporine Crystallization" Org. Process Res. Dev. 2017, 21, 1571-1587 (Year: 2017).*

"Continuous reactor" Wikipedia Jan. 13, 2018, captured Mar. 29, 2024 <https://en.wikipedia.org/w/index.php?title=Continuous_reactor&oldid=820217159>. (Year: 2018).*

Shakeel et al., Solubility and thermodynamic function of apremilast in different (Transcutol + water) cosolvent mixtures: Measurement, correlation and molecular interactions, J, Ind. Eng. Chem., 56:99-107 (2017).

Su et al., Pharmaceutical crystallisation processes from batch to continuous operation using MSMPR stages: Modelling, design, and control, Chem. Eng. and Proc., 89:41-53 (2015).

Wozniak et al., Preparation of Functionalized Alpha, Beta-Unsaturated Sulfonamides via Olefin Cross-Metathesis, Org. Lett., 22(13):4970-4973 (2020).

Jana et al., Synthesis of Substituted Beta-Functionalised Styrenes by Microwave-Assisted Olefin Cross-Metathesis and Scalable Synthesis of Apremilast, Chem. Cat. Chem., 11:5808-5813 (2019).

Jouyban et al., Preferential solvation of apremilast in some (Transcutol + water) mixtures, J. Mol. Liq., 316 (2):113905 (2020).

Kostrzewa et al., p-Philic Molecular Recognition in the Solid State as a Driving Force for Mechanochemical Formation of Apremilast Solvates and Cocrystals, Cryst. Growth Des., 18(7):3959-3970 (2018).

Lu et al., Identification and characterization of process-related substances and degradation products in apremilast: Process optimization and degradation pathway elucidation, J. Pharm. Biomed. Anal., 141:70-78 (2017).

Mandal et al., Domino Relay Olefin Metathesis of Triallyl Oxindole and Indole Precursors to Access Cyclic Indoxyls and Carbazoles, Chem. Cat. Chem., 12(19):4754-4759 (2020).

Syu et al., Asymmetric Synthesis of Beta-Aryl Beta-Imido Sulfones Using Rhodium Catalysts with Chiral Diene Ligands: Synthesis of Apremilast, Org. Lett., 21(12):4614-4618 (2019).

Trampuz et al., Catalyst-free aza-Michael addition for C-N coupling in active pharmaceutical ingredient synthesis: Modelling of thermodynamic, reaction kinetics and mass transfer considerations, Chem. Eng. J., 374:924-936 (2019).

* cited by examiner

*Primary Examiner* — Samantha L Shterengarts
*Assistant Examiner* — Jed A Kucharczk
(74) *Attorney, Agent, or Firm* — MARSHALL, GERSTEIN & BORUN LLP

(57) ABSTRACT

Provided herein are processes for synthesizing apremilast comprising reacting 3-acetamidophthalic anhydride and (S)-1-(3-ethoxy-4-methoxyphenyl)-2-(methylsulfonyl)ethan-1-amine or a salt thereof to form apremilast. Also provided are processes for isolating apremilast from the reaction mixture, as described herein.

31 Claims, 4 Drawing Sheets

PROCESS FOR SYNTHESIZING APREMILAST

FIELD OF THE DISCLOSURE

The disclosure provided herein relates to processes of synthesizing (+)-2-[1-(3-ethoxy-4-methoxyphenyl)-2-methylsulfonylethyl]-4-acetylaminoisoindoline-1,3-dione (apremilast), wherein embodiments of the process are drawn to a continuous process of synthesizing apremilast, and a batch process of synthesizing apremilast.

BACKGROUND

Apremilast is a member of the class of isoindolines that is substituted at position 4 by an acetamido group and at position 1 by a 1-(3-ethoxy-4-methoxyphenyl)-2-(methylsulfonyl)ethyl group. It has a role as a phosphodiesterase IV inhibitor and a non-steroidal anti-inflammatory drug, and has the following chemical structure:

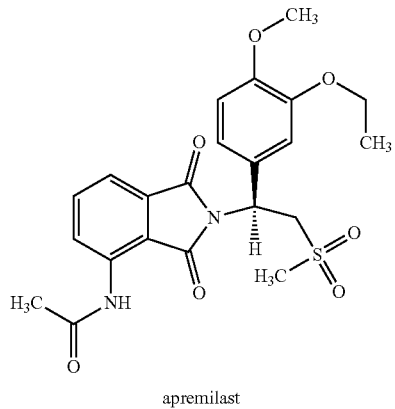

apremilast

Apremilast may be formed via an acid-catalysed condensation reaction between 3-acetamidophthalic anhydride (compound A) and (S)-1-(3-ethoxy-4-methoxyphenyl)-2-(methylsulfonyl)ethan-1-amine (compound B):

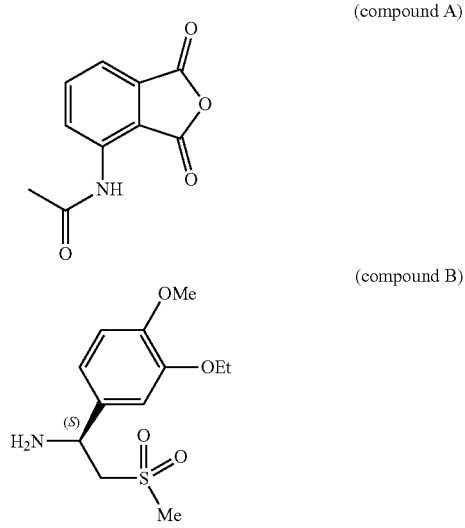

The reaction may proceed by various means. One such example is via an acid-catalyzed condensation of compound (A) with compound (B) in an organic solvent (e.g., tetrahydrofuran, THF) with a catalytic amount of water. The acid-catalyzed reaction requires the reaction mixture to be heated at 72° C. for about 16 hrs to yield crude apremilast. Isolation of the crude product from the reaction mixture then requires a series of aqueous workup steps, followed by a distillation process, and finally crystallization from a mixture of solvents such as isopropyl acetate/methyl tert-butyl ether.

A need exists for processes to generate apremilast that benefit from shorter cycle times due to an abbreviated reaction time, lesser waste generation via reduction in aqueous workup steps, and a smaller more flexible manufacturing footprint.

SUMMARY

Provided herein are methods of preparing apremilast comprising admixing (1) a first solution comprising 3-acetamidophthalic anhydride (Compound A) or a salt thereof in a first solvent and (2) a second solution comprising (S)-1-(3-ethoxy-4-methoxyphenyl)-2-(methylsulfonyl)ethan-1-amine (Compound B) or a salt thereof in a second solvent to form apremilast in a reaction mixture; and adding water to the reaction mixture to isolate the apremilast. In various embodiments, the admixing occurs in a plug-flow reactor.

In some embodiments, the admixing is performed in the presence of an acid. In some embodiments, the acid is an alkyl sulfonic acid, an aryl sulfonic acid, an alkyl carboxylic acid or an aryl carboxylic acid. In some embodiments, the acid is selected from the group consisting of acetic acid, methylsulfonic acid, tolylsulfonic acid, trifluoroacetic acid, trichloroacetic acid, dichloroacetic acid, chloroacetic acid, benzenesulfonic acid, triflic acid, ethylsulfonic acid, formic acid, propionic acid, benzoic acid, salicylic acid, and oxalic acid. In some embodiments, the acid comprises acetic acid. The acid can be present at 0.01 to 20 (or 0.5 to 3, or 1 to 2.5) volume equivalents based on Compound B or salt thereof.

In some embodiments, the admixing is performed in the presence of up to 1.5 (or 0.5) molar equivalents of water based on Compound B or salt thereof, while in other embodiments, the admixing is performed in the absence of water.

In various embodiments, Compound A or salt thereof is present at 0.4 to 1.5 (or 0.8 to 1.2, or at 0.99) molar equivalents based on Compound B or salt thereof. In various embodiments, Compound A is present as a neutral species (i.e., not in a salt form). In various embodiments, Compound B is present as a neutral species (i.e., not in salt form), while in other embodiments, Compound B is present in a salt form.

In various cases, the first and second solvents are the same solvent, while in other embodiments, the first and second solvents are different solvents. In various embodiments, the first and/or second solvent is a polar aprotic solvent. In various embodiments, the polar aprotic solvent has a boiling point of about 40° C. to about 200° C. at 1 atm. In various embodiments, the polar aprotic solvent has 0-10% by weight water, while in other embodiments, the polar aprotic solvent is anhydrous. In various embodiments, the polar aprotic solvent has a dielectric constant of 10 to 50 at room temperature and 1 atm. In various embodiments, the polar aprotic solvent is acetonitrile, dimethyl sulfoxide (DMSO), dimethylformamide (DMF), dimethylacetamide (DMAC), N-methyl-2-pyrrolidone (NMP), hexamethylphosphoramide (HMPA), N,N'-dimethylpropyleneurea (DMPU), sulfolane, dihydrolevoglucosenone, 1,3-dimethyl-2-imidazolidinone (DMI), or a combination thereof. In various embodiments, the polar aprotic solvent comprises DMSO.

In various embodiments, the admixing is performed at a temperature of 20° C. to 200° C., 50° C. to 200° C., 70° C. to 190° C., 130° C. to 135° C., or at 70° C. to reflux of the solvent. In some embodiments, the admixing occurs at a reaction time of 0.1 min to 48 hrs, or 4 hrs to 36 hrs, or 8 hrs to 24 hrs, or 16 hrs. In some embodiments, the admixing occurs at a residence time of 0.1 min to 120 min, or 1 min to 60 min, or 10 min to 40 min, or 15 min to 30 min, or 25 min to 30 min. In some embodiments, the admixing occurs at a residence time of 35 minutes.

In various embodiments, the isolation comprises (a) cooling said reaction mixture to a temperature of 0° C. to 50° C. to form a cooled solution; (b) adding water to said cooled solution; and (c) precipitating said apremilast from said solution formed in step (b) to isolate said apremilast. In various embodiments, the methods further comprise filtering the precipitated apremilast of step (c). In various embodiments, step (b) further comprises adding crystalline apremilast to said cooled solution such that said precipitating of step (c) results in crystalline apremilast.

In various embodiments, the isolation comprises continuous crystallization using mixed-suspension, mixed-product removal (MSMPR) crystallizers; parallel filtration, or a combination thereof.

Also provided are methods of isolating apremilast from a reaction mixture comprising crude apremilast and DMSO, comprising: (a) cooling said reaction mixture to a temperature of 0° C. to 50° C. to form a cooled solution; (b) adding water to said cooled solution; (c) precipitating apremilast from said solution formed in step (b) to form precipitated apremilast; and (d) isolating said precipitated apremilast. In various embodiments, the isolation is by filtering. In various embodiments, step (b) further comprises adding crystalline apremilast to said cooled solution. In various embodiments, the precipitated apremilast is crystalline.

Also provided are methods of preparing apremilast comprising (a) admixing (1) a first solution comprising 3-acetamidophthalic anhydride (Compound A) in a first solvent and (2) a second solution comprising (S)-1-(3-ethoxy-4-methoxyphenyl)-2-(methylsulfonyl)ethan-1-amine (Compound B) or a salt thereof in a second solvent to form apremilast in a reaction mixture, wherein the admixing occurs in a continuous process apparatus; and (b) isolating said apremilast from said reaction mixture, wherein said isolating comprises: (i) cooling the reaction mixture to a temperature of 0° C. to 50° C.; (ii) adding water to the cooled reaction mixture; (iii) precipitating apremilast from the mixture of step (ii); and (iv) isolating said precipitated apremilast.

Also provided are processes of preparing crystalline apremilast, comprising: (a) admixing (1) a first solution comprising 3-acetamidophthalic anhydride (Compound A) in a first solvent and (2) a second solution comprising (S)-1-(3-ethoxy-4-methoxyphenyl)-2-(methylsulfonyl)ethan-1-amine (Compound B) or a salt thereof in a second solvent to form apremilast in a reaction mixture, wherein the admixing occurs in a continuous process apparatus; and (b) isolating crystalline apremilast from said reaction mixture by continuous crystallization and parallel filtration. In various embodiments, the continuous crystallization comprises using mixed-suspension, mixed-product removal (MSMPR) crystallizers.

DETAILED DESCRIPTION

Figure 1:
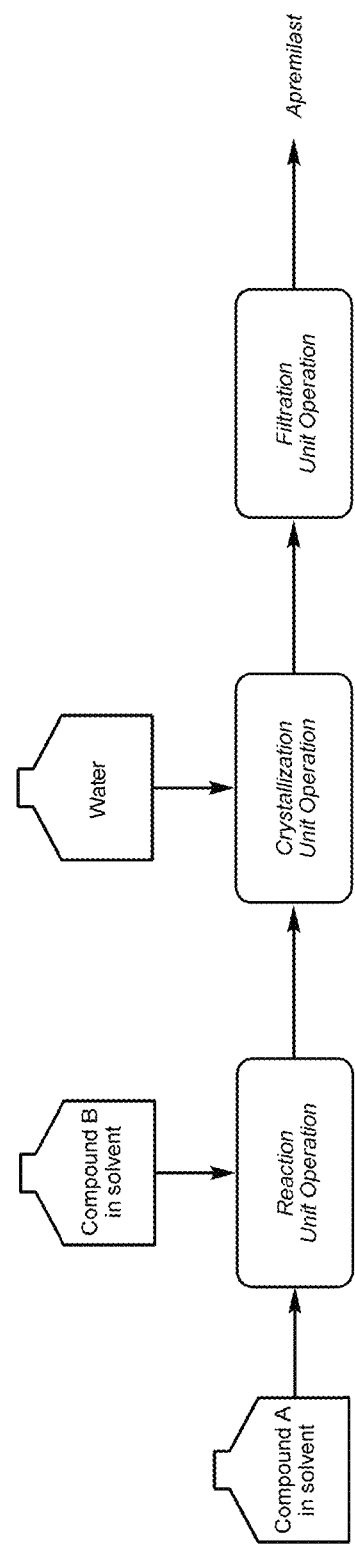
FIG. 1 depicts a process flow diagram for a continuous reaction process and continuous crystallization of apremilast as disclosed herein.

The following discussion is directed to various exemplary embodiments of the disclosed processes.

However, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and that the scope of this disclosure, including the claims, is not limited to that embodiment.

As used herein, the terms "including" and "comprising" are used in an open-ended fashion, and thus should be interpreted to mean "including, but not limited to . . . ." As used herein, the term "about," when used in conjunction with a percentage or other numerical amount, means plus or minus 10% of that percentage or other numerical amount. For example, the term "about 80%," would encompass 80% plus or minus 8%.

Processes of Synthesizing Apremilast

Provided herein are processes for obtaining apremilast. Further provided herein are processes for isolating and crystallizing apremilast.

In some embodiments, the disclosure provides processes of preparing apremilast comprising admixing (1) a first solution comprising 3-acetamidophthalic anhydride (compound A) or a salt thereof in a first solvent, and (2) a second solution comprising (S)-1-(3-ethoxy-4-methoxyphenyl)-2-(methylsulfonyl)ethan-1-amine (compound B) or a salt thereof in a second solvent to form apremilast in a reaction mixture; and adding water to the reaction mixture to isolate the apremilast. In some embodiments, the process of synthesizing apremilast is a continuous reaction process. In some embodiments, the process of synthezising apremilast is a batch process.

In some embodiments, a continuous process (or continuous manufacture (CM)) involves: a) the continuous feeding of input materials into, b) the continuous transformation of in-process materials within, and/or c) the continuous removal of output materials from a process. In some embodiments of a continuous process, two or more unit operations are directly connected, wherein a unit operation may be defined as a basic step in a process involving a physical change or chemical transformation such as but not limited to a reaction, crystallization, distillation, and purification. In some embodiments, a continuous process can be applied to some or all unit operations.

A continuous process may comprise a combination of manufacturing approaches, wherein some unit operations operate in a batch mode while others are integrated and operate in a continuous mode. In some cases, the process is integrated and operates in a continuous mode. In some embodiments, the continuous reaction process may incorporate surge lines or tanks to maintain a constant flow of material inputs and outputs in any mode of a continuous reaction process described herein.

In some embodiments, continuous reaction processes are sequences of chemical transformations, solvent changes, purification steps, etc. that may comprise the integration of typical unit operations used in drug substance processes into a continuous process. The integrated process may in some embodiments comprise a plug-flow reactor (PFR), wherein for example PFR design elements (e.g., dimension and configuration) allow precise control of temperature, mixing and reactant flows, continuous stirred tank reactor (CSTR), homogeneous and heterogeneous phase extractions, continuous crystallization, and/or filtration. In some embodiments, starting materials may be coupled in a PFR to produce a crude product; the crude product may be purified by extraction and continuous crystallization. A crystal slurry may be filtered by using units running in an alternating fashion, allowing continuous processing of the drug substance after crystallization.

Starting Materials/Reactants

In the disclosed processes, a solution of Compound A or salt thereof and a solution of Compound B or salt thereof are admixed together to form apremilast. In some cases, Compound A can be present as a neutral species (i.e., not as a salt). In some cases, Compound A can be present as a salt form. In some embodiments, the salt form of Compound A can be an alkali metal or alkaline earth metal salt. Some specifically contemplated salt forms include, but are not limited to, calcium, magnesium, sodium, lithium, zinc, potassium, and iron salts. In some cases, Compound B can be present as a free base (i.e., not as a salt), as a neutral amine compound. In some cases, Compound B can be present as a salt form. In some embodiments, the salt form of Compound B can be an acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, leucinate, napsylate, nitrate, panthothenate, phosphate/diphosphate, polygalacturonate, salicylate, stearate, succinate, sulfate, tannate, tartrate, teoclate, triethiodide, or pamoate.

Compound A or salt thereof can be present in 10 molar equivalents or less based on Compound B or salt thereof; for example 9.5 molar equivalents, 9 molar equivalents, 8.5 molar equivalents, 8 molar equivalents, 7.5 molar equivalents, 7 molar equivalents, 6.5 molar equivalents, 6 molar equivalents, 5.5 molar equivalents, 5 molar equivalents, 4.5 molar equivalents, 4 molar equivalents, 3.5 molar equivalents, 3 molar equivalents, 2.5 molar equivalents, 2 molar equivalents, 1.5 molar equivalents, 1 molar equivalents, 0.5 molar equivalents, 0.4 molar equivalents, 0.3 molar equivalents, 0.2 molar equivalents, or 0.1 molar equivalents or less. Alternatively, or in addition to, in various embodiments, the disclosure provides processes of preparing apremilast wherein Compound A or salt thereof is present at 0.1 molar equivalents or more based on Compound B or salt thereof, for example: 0.1 molar equivalents, 0.2 molar equivalents, 0.3 molar equivalents, 0.4 molar equivalents, 0.5 molar equivalents, 1 molar equivalents, 1.5 molar equivalents, 2 molar equivalents, 2.5 molar equivalents, 3 molar equivalents, 3.5 molar equivalents, 4 molar equivalents, 4.5 molar equivalents, 5 molar equivalents, 6 molar equivalents, 6.5 molar equivalents, 7 molar equivalents, 7.5 molar equivalents, 8 molar equivalents, 8.5 molar equivalents, 9 molar equivalents, 9.5 molar equivalents, or 10 molar equivalents or more. Thus, in some embodiments, the disclosure provides processes of preparing apremilast, wherein Compound A or salt thereof can be present in an amount bound by, and including, any combination of the aforementioned endpoints. In various embodiments, the disclosure provides processes of preparing apremilast, wherein Compound A or salt thereof is present at 0.4 to 1.5 molar equivalents based on Compound B or salt thereof. In some other embodiments, Compound A or salt thereof is present at 0.8 to 1.2 molar equivalents based on Compound B or salt thereof. In some embodiments, Compound A or salt thereof is present at 0.99 molar equivalents based on Compound B or salt thereof.

Solvents

The solution of Compound A or salt thereof is in a first solvent. The solution of Compound B or salt thereof is in a second solvent. In some embodiments, the first solvent and the second solvent are the same solvent. In some other embodiments, the first solvent and the second solvent are different solvents.

The first and/or second solvent is any solvent compatible with the condensation reaction to form apremilast. For example, the solvent may be selected for its stability at the operating temperatures of the disclosed process. Thus, the solvent may be selected to have minimal or no thermal decomposition under the conditions of the process. The solvent selected may be selected such that it does not negatively interact with the reactants, intermediate species, or product of the process, nor reduce the yield of apremilast. The solvent may be selected to increase the solubility of reactants (compounds A and/or B) allowing for improved homogeneity of the reaction mixture. The solvent may promote accelerated reaction kinetics by facilitating safe operation at high temperatures. The solvent may also allow direct crystallization of apremilast from the reactant mixture (e.g., by the addition of water).

In various embodiments, the solvent is a polar aprotic solvent. As used herein, "polar aprotic solvent" refers to a solvent lacking O—H or N—H bonds, having a dielectric constant (E) of greater than 6, and a dipole moment of greater than 1.5 D, when measured at 20 to 25° C. (room temperature). In some embodiments, the polar aprotic solvent has a dielectric constant of 10 to 60 at room temperature and 1 atmosphere. In some embodiments, the polar aprotic solvent has a dielectric constant of 20 to 55 at room temperature and 1 atmosphere; In some embodiments, the polar aprotic solvent has a dielectric constant of 30 to 50 at room temperature and 1 atmosphere.

The solvent can have any suitable boiling point provided that the solvent is stable under the conditions of the process (e.g., reaction temperatures and pressures) such that the solvent does not undergo significant thermal decomposition. In some embodiments, the polar aprotic solvent has a boiling point of about 40° C. to about 200° C. at 1 atmosphere. The solvent can have a boiling point of 40° C. or more, for example, 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., or 200° C. or more. Alternatively, or in addition to, in various embodiments, the solvent can have a boiling point of 200° C. or less, for example 195° C., 190° C., 185° C., 180° C., 175° C., 170° C., 165° C., 160° C., 155° C., 150° C., 145° C., 135° C., 130° C., 125° C., 120° C., 115° C., 110° C., 110° C., 105° C., 100° C., 95° C., 90° C., 85° C., 80° C., 75° C., 75° C., 70° C., 65° C., 60° C., 55° C., 50° C., or 45° C., or less. Thus, in some embodiments, the boiling point of a chosen solvent may comprise a temperature bound by, and including, any combination of the aforementioned endpoints.

In some embodiments, the polar aprotic solvent has 10% by weight water or less for example 9%, 8%, 7%, 6%, 5%, 4%, 3%, 2%, or 1% or less. In some specific embodiments, the polar aprotic solvent is anhydrous.

Specifically contemplated polar aprotic solvents for use in the disclosed processes include acetonitrile, dimethyl sulfoxide (DMSO), dimethylformamide (DMF), dimethylacetamide (DMAC), N-methyl-2-pyrrolidone (NMP), hexamethylphosphoramide (HMPA), N,N-dimethylpropyleneurea (DMPU), sulfolane, dihydrolevoglucosenone, 1,3-dimethyl-2-imidazolidinone (DMI), or a combination thereof. In some embodiments, the polar aprotic solvent comprises dimethyl sulfoxide (DMSO). Use of polar aprotic solvents such as DMSO as a reaction solvent has been shown to provide the following improvements: 1) accelerated reaction kinetics via safe operation at high temperature, 2) increased solubility of reaction components allowing for homogeneous reaction solutions, 3) direct crystallization of apremilast from the crude reaction stream, obviating the need for time- and resource-consuming downstream processing steps.

Other Additives for Disclosed Processes

In some embodiments, the disclosed processes can be performed in the presence of an acid. In some embodiments, the acid is an alkyl sulfonic acid, an aryl sulfonic acid, an alkyl carboxylic acid or an aryl carboxylic acid. In some embodiments, the acid is selected from the group consisting of acetic acid, methylsulfonic acid, tolylsulfonic acid, trifluoroacetic acid, trichloroacetic acid, dichloroacetic acid, chloroacetic acid, benzenesulfonic acid, triflic acid, ethylsulfonic acid, formic acid, propionic acid, benzoic acid, salicylic acid, and oxalic acid. In some embodiments, the acid comprises acetic acid.

The acid can be present in 20 volume equivalents or less based on Compound B or salt thereof, for example, 20 volume equivalents, 19.5 volume equivalents, 19 volume equivalents, 18.5 volume equivalents, 18 volume equivalents, 17.5 volume equivalents, 17 volume equivalents, 16.5 volume equivalents, 16 volume equivalents, 15.5 volume equivalents, 14 volume equivalents, 13.5 volume equivalents, 13 volume equivalents, 12.5 volume equivalents, 12 volume equivalents, 11.5 volume equivalents, 11 volume equivalents, 10.5 volume equivalents, 10 volume equivalents, 9.5 volume equivalents, 9 volume equivalents, 8.5 volume equivalents, 8 volume equivalents, 7.5 volume equivalents, 7 volume equivalents, 6.5 volume equivalents, 6 volume equivalents, 5.5 volume equivalents, 5 volume equivalents, 4.5 volume equivalents, 4 volume equivalents, 3.5 volume equivalents, 3 volume equivalents, 2.5 volume equivalents, 2 volume equivalents, 1.5 volume equivalents, 1 volume equivalents, 0.5 volume equivalents, 0.4 volume equivalents, 0.3 volume equivalents, 0.2 volume equivalents, or 0.1 volume equivalents. Alternatively, or in addition to, in various embodiments, the acid is present at 0.01 volume equivalents or more based on Compound B or salt thereof, for example 0.1 volume equivalents, 0.2 volume equivalents, 0.3 volume equivalents, 0.4 volume equivalents, 0.5 volume equivalents, 1 volume equivalents, 1.5 volume equivalents, 2 volume equivalents, 2.5 volume equivalents, 3 volume equivalents, 3.5 volume equivalents, 4 volume equivalents, 4.5 volume equivalents, 5 volume equivalents, 6 volume equivalents, 6.5 volume equivalents, 7 volume equivalents, 7.5 volume equivalents, 8 volume equivalents, 8.5 volume equivalents, 9 volume equivalents, 9.5 volume equivalents, 10 volume equivalents, 10.5 volume equivalents, 11 volume equivalents, 11.5 volume equivalents, 12 volume equivalents, 12.5 volume equivalents, 13 volume equivalents, 13.5 volume equivalents, 14 volume equivalents, 14.5 volume equivalents, 15 volume equivalents, 15.5 volume equivalents, 16 volume equivalents, 16.5 volume equivalents, 17 volume equivalents, 17.5 volume equivalents, 18 volume equivalents, 18.5 volume equivalents, 19 volume equivalents, 19.5 volume equivalents, or 20 volume equivalents based on Compound B or salt thereof. Thus, in some embodiments, the acid may be present at a volume equivalent based on Compound B or salt thereof, including any combination of the aforementioned endpoints. For example, the acid is present at 0.01 to 20 volume equivalents based on Compound B or salt thereof. In some cases, the acid is present at 0.1 to 10 volume equivalents based on Compound B or salt thereof. In some cases, the acid is present at 0.5 to 3 volume equivalents based on Compound B or salt thereof. In some cases, the acid is present at 1 to 2.5 volume equivalents based on Compound B or salt thereof.

The acid can be present in 20 molar equivalents or less based on Compound B or salt thereof, for example, 20 molar equivalents, 19.5 molar equivalents, 19 molar equivalents, 18.5 molar equivalents, 18 molar equivalents, 17.5 molar equivalents, 17 molar equivalents, 16.5 molar equivalents, 16 molar equivalents, 15.5 molar equivalents, 14 molar equivalents, 13.5 molar equivalents, 13 molar equivalents, 12.5 molar equivalents, 12 molar equivalents, 11.5 molar equivalents, 11 molar equivalents, 10.5 molar equivalents, 10 molar equivalents, 9.5 molar equivalents, 9 molar equivalents, 8.5 molar equivalents, 8 molar equivalents, 7.5 molar equivalents, 7 molar equivalents, 6.5 molar equivalents, 6 molar equivalents, 5.5 molar equivalents, 5 molar equivalents, 4.5 molar equivalents, 4 molar equivalents, 3.5 molar equivalents, 3 molar equivalents, 2.5 molar equivalents, 2 molar equivalents, 1.5 molar equivalents, 1 molar equivalents, 0.5 molar equivalents, 0.4 molar equivalents, 0.3 molar equivalents, 0.2 molar equivalents, or 0.1 molar equivalents. Alternatively, or in addition to, in various embodiments, the acid is present at 0.01 molar equivalents or more based on Compound B or salt thereof, for example 0.1 molar equivalents, 0.2 molar equivalents, 0.3 molar equivalents, 0.4 molar equivalents, 0.5 molar equivalents, 1 molar equivalents, 1.5 molar equivalents, 2 molar equivalents, 2.5 molar equivalents, 3 molar equivalents, 3.5 molar equivalents, 4 molar equivalents, 4.5 molar equivalents, 5 molar equivalents, 6 molar equivalents, 6.5 molar equivalents, 7 molar equivalents, 7.5 molar equivalents, 8 molar equivalents, 8.5 molar equivalents, 9 molar equivalents, 9.5 molar equivalents, 10 molar equivalents, 10.5 molar equivalents, 11 molar equivalents, 11.5 molar equivalents, 12 molar equivalents, 12.5 molar equivalents, 13 molar equivalents, 13.5 molar equivalents, 14 molar equivalents, 14.5 molar equivalents, 15 molar equivalents, 15.5 molar equivalents, 16 molar equivalents, 16.5 molar equivalents, 17 molar equivalents, 17.5 molar equivalents, 18 molar equivalents, 18.5 molar equivalents, 19 molar equivalents, 19.5 molar equivalents, or 20 molar equivalents based on Compound B or salt thereof. Thus, in some embodiments, the acid may be present at a molar equivalent based on Compound B or salt thereof, including any combination of the aforementioned endpoints. For example, the acid is present at 0.01 to 20 molar equivalents based on Compound B or salt thereof. In some cases, the acid is present at 0.1 to 15 molar equivalents based on Compound B or salt thereof. In some cases, the acid is present at 5 to 12 molar equivalents based on Compound B or salt thereof. In some cases, the acid is present at 11 to 12 molar equivalents based on Compound B or salt thereof.

In some embodiments, the admixing is performed in the presence of up to 1.5 molar equivalents of water based on Compound B or salt thereof; in some embodiments, up to 1.25 molar equivalents of water is present, based on Compound B or salt thereof. In some embodiments, up to 1 molar equivalents of water is present, based on Compound B or salt thereof. In some embodiments, up to 0.75 molar equivalents of water is present based on Compound B or salt thereof. In some embodiments, the water is present at 0.5 molar equivalents based on Compound B or salt thereof. In various embodiments, the water is present at 0.25 molar equivalents based on Compound B or salt thereof. In some embodiments, water is not present.

Temperature

The processes for preparing apremilast, as disclosed herein, may occur over a range of temperatures. The disclosed processes can occur at elevated temperatures, compared to prior syntheses of apremilast, which provides a shorter reaction time, such as the reaction can occur over hours or minutes vs. days. Synthesizing apremilast as described herein is therefore practicable, proceeding to a suitable yield, and is particularly amenable to industrial scale-up, resulting in cost savings and solvent waste reduction associated with these processes. Thus, in some embodiments, the disclosure provides processes of preparing apremilast, wherein the admixing of Compounds A and B as discussed above may be performed at a temperature of 20° C. to 200° C. In some embodiments, the admixing is performed at a temperature of 70° C. to reflux of the solvent. In some embodiments, the admixing is performed at a temperature of 50° C. to 200° C. In some embodiments, the admixing is performed at a temperature of 70° C. to 190° C. In various embodiments, the admixing is performed at a temperature of 130° C. to 135° C. In various embodiments, the admixing is performed at a temperature of 20° C. or more, for example, 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., or 210° C. or more. Alternatively, or in addition to, in various embodiments, the disclosure provides processes of preparing Apremilast wherein the admixing is performed to a temperature of 210° C. or less, for example, 205° C., 200° C., 195° C., 190° C., 185° C., 180° C., 175° C., 170° C., 165° C., 160° C., 155° C., 150° C., 145° C., 135° C., 130° C., 125° C., 120° C., 115° C., 110° C., 110° C., 105° C., 100° C., 95° C., 90° C., 85° C., 80° C., 75° C., 75° C., 70° C., 65° C., 60° C., 55° C., 50° C., 45° C., 40° C., 35° C., 30° C. or less. Thus, in some embodiments, the disclosure provides processes of preparing apremilast, wherein the admixing is performed at a temperature bound by, and including, any combination of the aforementioned endpoints.

Reaction Time

The processes for preparing apremilast, as disclosed herein, may occur over a range of reaction times, and provide a commercially relevant reaction time. In some embodiments, the admixing of Compounds A and B, as discussed above, occurs at a mean reaction time of 0.1 minute to 48 hrs. In some embodiments, the admixing occurs at a mean reaction time of 4 hr to 36 hours. In some embodiments, the admixing occurs at a mean reaction time of 8 to 24 hrs. In some embodiments, the admixing occurs at a mean reaction time of 16 hrs. In various embodiments, the admixing occurs for 5 minutes to 16 hours, for example, 15, 30, or 45 minutes or more. In some cases, the admixing occurs for 16 hours or less, for example, 15.5 hours or less, 15 hours or less, 14.5 hours or less, 14 hours or less, 13.5 hours or less, 13 hours or less, 12.5 hours of less, 12 hours or less, 11.5 hours or less, 11 hours or less, 10.5 hours or less, 10 hours or less, 9.5 hours or less, 9 hours or less, 8.5 hours or less, 8 hours or less, 7.5 hours or less, 7 hours or less, 6.5 hours or less, 6 hours or less, 5.5 hours or less, 5 hours or less, 4.5 hours or less, 4 hours or less, 3.5 hours or less, 3 hours or less, 2.5 hours or less, 2 hours or less, 1.5 hours or less, or 1 hour or less. In various embodiments, the admixing occurs for 1 to 4 hours.

Residence Time

In certain embodiments, the admixing occurs as a continuous reaction process. For example, the reaction can occur in a plug-flow reactor (PFR). A plug flow reactor may be used in continuous reaction processes, wherein the concentration and temperature of the reactants (such as compound A or salt thereof in a first solvent and compound B or salt thereof in a second solvent) are uniform. A plug flow reactor has a fixed residence time (–). The reaction mixture going through a PFR may be treated as flowing through the reactor as a series of coherent "plugs", wherein each plug has a uniform composition, which travels only in the axial direction of the reactor. As a plug flows through a PFR, the reaction mixture is admixed in the radial direction. The mean residence time ($\tau$) in the PFR is the average time in which the reaction components spend in the PFR. Residence time is indicative of what would otherwise be considered a "reaction time" for a conventional or batch process.

The processes for preparing apremilast, as disclosed herein, may occur over a range of residence times. The residence time can be 120 minutes or less; for example: 115 minutes; 110 minutes; 105 minutes; 100 minutes; 95 minutes; 90 minutes; 85 minutes; 80 minutes; 75 minutes; 70 minutes; 65 minutes; 60 minutes; 55 minutes; 50 minutes; 45 minutes; 40 minutes; 35 minutes; 30 minutes; 25 minutes; 20 minutes; 15 minutes; 10 minutes; 5 minutes; 1 minute; 0.9 minutes; 0.8 minutes; 0.7 minutes; 0.6 minutes; 0.5 minutes; 0.4 minutes; 0.3 minutes; 0.2 minutes; or 0.1 minutes or less. Alternatively, or in addition to, in various embodiments, the residence time can be 0.1 minutes or more, for example 0.1 minutes; 0.2 minutes; 0.3 minutes; 0.4 minutes; 0.5 minutes; 0.6 minutes; 0.7 minutes; 0.8 minutes; 0.9 minutes; 1 minute; 1.5 minutes; 2 minutes; 2.5 minutes; 3 minutes; 3.5 minutes; 4 minutes; 4.5 minutes; 5 minutes; 10 minutes; 15 minutes; 20 minutes; 25 minutes; 30 minutes; 35 minutes; 40 minutes; 45 minutes; 50 minutes; 55 minutes; 60 minutes; 65 minutes; 70 minutes; 75 minutes; 80 minutes; 85 minutes; 90 minutes; 95 minutes; 100 minutes; 110 minutes; 115 minutes; or 120 minutes or more. Thus, in some embodiments, the admixing is performed at residence time bound by, and including, any combination of the aforementioned endpoints. In various embodiments, the admixing occurs at a residence time of 0.1 to 120 minutes, or 1 minute to 60 minutes; or 10 minutes to 40 minutes; or 15 minutes to 30 minutes; or 25 minutes to 30 minutes, or 25 minutes to 35 minutes.

Isolating Apremilast

A comparative method for preparing apremilast from Compound A and Compound B was performed in tetrahydrofuran (see e.g., Example 9 in the Examples section below for a typical procedure using tetrahydrofuran). The process requires a long reaction time (at least 16 h at 70 to 75° C.).

Isolation of crude apremilast from the THF reaction mixture requires a series of aqueous workup steps, followed by a distillation process, and finally crystallization from a mixture of solvents such as isopropyl acetate and methyl tert-butyl ether. In view of the foregoing, the present disclosure provides processes that both readily isolate apremilast directly from the reaction mixture and produce crystalline apremilast.

Therefore, in some embodiments, the disclosure provides processes of preparing apremilast which further comprise adding water to the reaction mixture to isolate apremilast. In some embodiments, isolating apremilast from the reaction mixture comprises: (a) cooling the reaction mixture to a temperature of 0° C. to 50° C. to form a cooled solution; (b) adding water to the cooled solution; and (c) precipitating the apremilast from the solution formed in step (b) to isolate the apremilast. In some embodiments, the processes further comprise filtering the precipitated apremilast of step (c). In some embodiments, step (b) further comprises adding crystalline apremilast to the cooled solution such that the precipitating of step (c) results in crystalline apremilast. In some embodiments, the isolating comprises continuous crystallization using a mixed-suspension, mixed-product removal (MSMPR) crystallizer, parallel filtration, or a combination thereof.

Cooling the Reaction Mixture

The cooling of step (b) is at a temperature of 0° C. or more, for example, 5° C., 10° C., 15° C., 20° C., 25° C., 30° C., 35° C., 40° C., or 45° C. or more. Alternatively, or in addition to, in various embodiments, the cooling is at a temperature of 50° C. or less, for example, 45° C., 40° C., 35° C., 30° C., 25° C., 20° C., 15° C., 10° C., or less. Thus, in some embodiments, cooling the reaction mixture is at a temperature bound by, and including, any combination of the aforementioned endpoints. In some cases, the cooling comprises cooling the admixture to room temperature (20 to 25° C.).

It has surprisingly been found and disclosed herein, that the implementation of DMSO as a reaction solvent provides for a number of process improvements including facilitating the direct crystallization of crude apremilast from the reaction mixture (or reaction stream) thereby obviating the need for time and resource-consuming downstream processing steps. Seeding the reaction mixture with crystalline apremilast additionally allows for the precipitation of crystalline apremilast. Thus, in some embodiments, the disclosure provides a process for isolating apremilast from a reaction mixture comprising crude apremilast and DMSO, comprising (a) cooling the reaction mixture to a temperature of 0° C. to 50° C. to form a cooled solution; (b) adding water to the cooled solution; (c) precipitating apremilast from the solution formed in step (b) to form precipitated apremilast; and (d) isolating the precipitated apremilast. In some embodiments, step (b) further comprises adding crystalline apremilast to the cooled solution; such that the precipitated apremilast is crystalline.

Figure 3A:
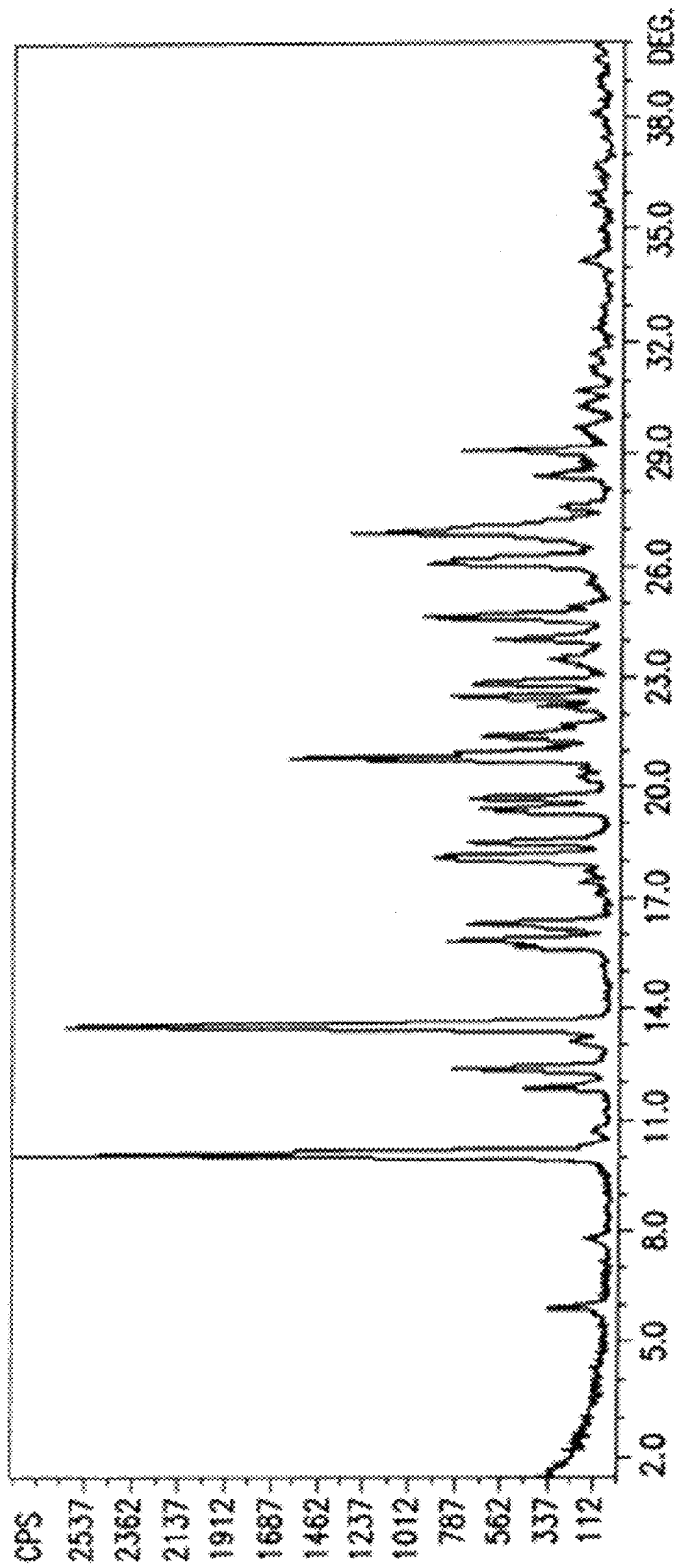
FIG. 3A depicts a XRPD plot of crystal Form B of apremilast as disclosed herein.
Figure 3B:
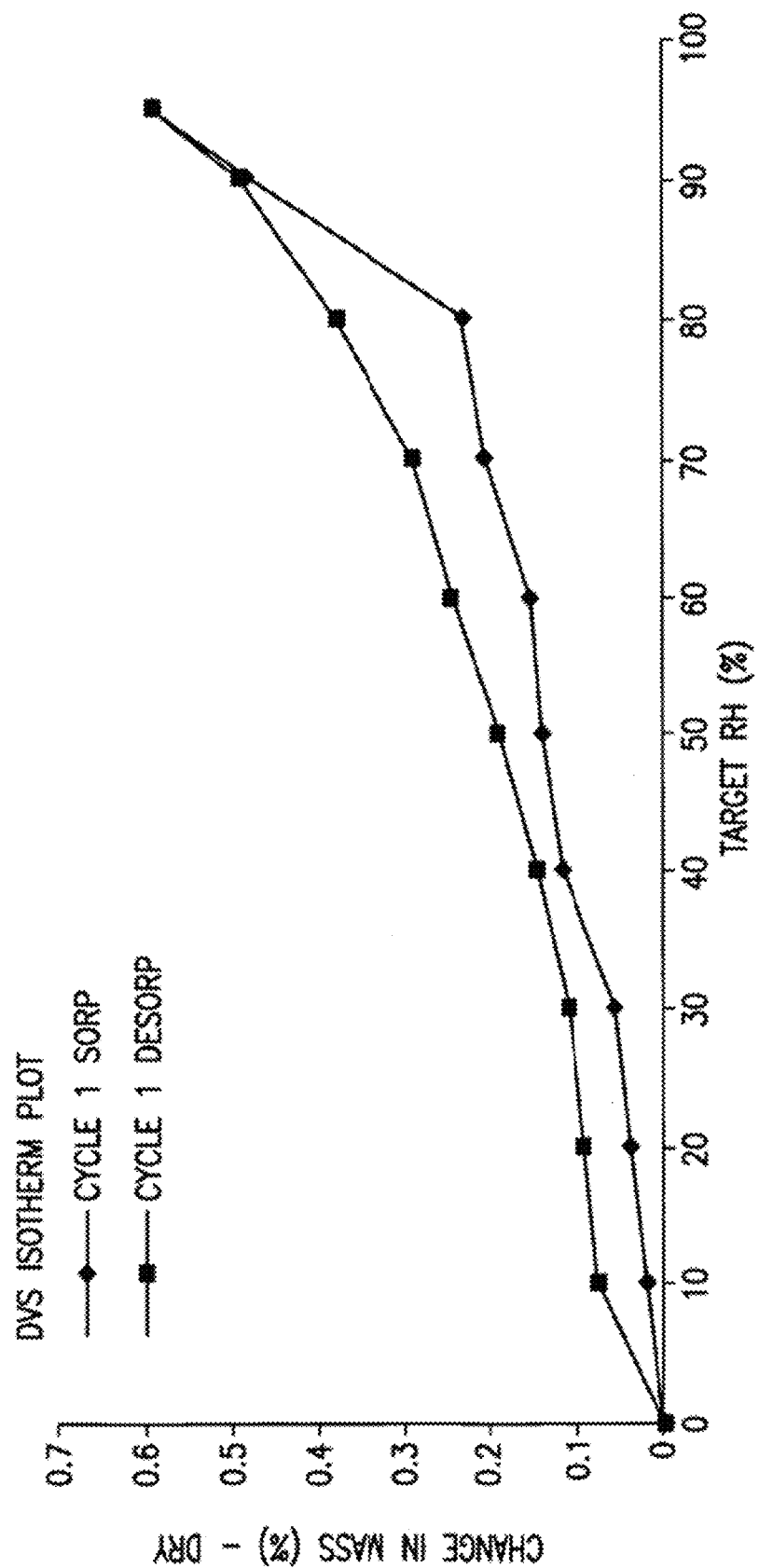
FIG. 3B depicts a representative DVS plot of crystal Form B of apremilast.

The crystalline apremilast formed in the disclosed processes can be any crystalline form. Various crystalline apremilast forms are described in detail in PCT Publication No. WO 2009/120167, the disclosure of which is incorporated by reference in its entirety. In various embodiments, the crystalline apremilast formed by the processes disclosed herein can be Form A, Form B, or Form F. In some cases, the crystalline apremilast is Form B. Form B may be characterized by X-ray powder diffraction analysis. A representative XRPD pattern of Form B is provided in FIG. 3. In certain embodiments, Form B is characterized by XRPD peaks located at one, two, three, four, five, six, seven, eight, nine, ten, eleven or twelve of the following approximate positions: 10.1, 12.4, 13.5, 15.7, 16.3, 18.1, 20.7, 22.5, 24.7, 26.2, 26.9, 29.1 degrees 2θ. In certain embodiments, Form B is characterized by an XRPD pattern which matches the pattern exhibited in FIG. 3. In certain embodiments, Form B may be characterized by thermal analysis. A representative DSC plot for Form B is shown in FIG. 3. In certain embodiments, Form B is characterized by a DSC plot comprising an endothermic event with an onset temperature of about 154° C. A representative TGA plot for Form B is shown in FIG. 3. In certain embodiments, Form B is characterized by a TGA plot comprising a mass loss of less than about 1%, e.g., about 0.25%, of the total mass of the sample upon heating from about 25° C. to about 140° C. In certain embodiments, Form B does not contain substantial amounts of either water or other solvent in the crystal lattice. In certain embodiments, Form B is anhydrous. In certain embodiments, Form B is unsolvated. In certain embodiments, Form B may be characterized by moisture sorption analysis. A representative moisture sorption isotherm plot is shown in FIG. 3b. In certain embodiments, when the RH is increased from about 0% to about 95% RH, Form B exhibits a mass change of less than about 1%, e.g., about 0.6%, of the starting mass of the sample. In certain embodiments, mass gained upon adsorption is lost when the RH is decreased back to about 0% RH. In certain embodiments, Form B is substantially nonhygroscopic. In certain embodiments, the XRPD pattern of Form B material is substantially unchanged following the adsorption/desorption analysis. In certain embodiments, Form B is stable with respect to humidity.

The continuous reaction process as disclosed herein, is an effective method for producing apremilast in part because the reactants (compound A and compound B) are readily soluble in polar aprotic solvents such as DMSO, and thereby provides a reaction stream that is suitable for use in a PFR. The reaction stream enters the PFR and the reaction is facilitated over a suitable residence time and temperature within the PFR. The reaction stream comprising crude apremilast then may undergo continuous crystallization which comprises using mixed-suspension, mixed-product removal (MSMPR) crystallizers. These continuous reaction processes, then, allow for the isolation of crystalline apremilast without need of intermediate isolation of crude apremilast or multiple solvent washes, or the like, which reduces reaction costs and production time.

In some embodiments, a reaction stream comprising crude apremilast and water is mixed in a MSMPR along with crystalline apremilast for seeded crystallization to provide crystalline apremilast. Thus, in some embodiments, the disclosure provides a process of preparing apremilast which comprises reacting compound A or salt thereof and compound B or salt thereof as discussed above, such that the reaction occurs in a continuous reaction process apparatus wherein crude apremilast is formed in the reaction mixture; and the process further comprises isolating apremilast from the reaction mixture. In various cases, the isolating comprises cooling the reaction mixture to a temperature of 0° C. to 50° C.; adding water to the cooled reaction mixture; precipitating apremilast from the cooled reaction mixture; and isolating the precipitated apremilast.

In some embodiments, the disclosure provides processes of preparing crystalline apremilast, comprising: a) admixing (1) a first solution comprising compound A or salt thereof in a first solvent and (2) a second solution comprising compound B or a salt thereof in a second solvent to form apremilast in a reaction mixture, wherein the admixing occurs in a continuous reaction process apparatus; and (b) isolating crystalline apremilast from the reaction mixture by continuous crystallization and parallel filtration. In various cases, the isolation of crystalline apremilast can comprise using mixed-suspension, mixed-product removal (MSMPR) crystallizers.

EMBODIMENTS

1. A process of preparing apremilast comprising:
   admixing (1) a first solution comprising 3-acetamidophthalic anhydride (Compound A) or a salt thereof in a first solvent and (2) a second solution comprising (S)-1-(3-ethoxy-4-methoxyphenyl)-2-(methylsulfonyl)ethan-1-amine (Compound B) or a salt thereof in a second solvent to form apremilast in a reaction mixture; and
   adding water to the reaction mixture to isolate the apremilast.
2. The process of embodiment 1, wherein Compound A or salt thereof is present at 0.4 to 1.5 molar equivalents based on Compound B or salt thereof.
3. The process of embodiment 2, wherein Compound A or salt thereof is present at 0.8 to 1.2 molar equivalents based on Compound B or salt thereof.
4. The process of embodiment 3, wherein Compound A or salt thereof is present at 0.99 molar equivalents based on Compound B or salt thereof.
5. The process of any one of embodiments 1-4, wherein Compound A in not in salt form.
6. The process of any one of embodiments 1-5, wherein said first solvent and said second solvent are the same solvent.
7. The process of any one of embodiments 1-6, wherein said first solvent and said second solvent are different solvents.
8. The process of any one of embodiments 1-7, wherein said first solvent is a polar aprotic solvent.
9. The process of any one of embodiments 1-8, wherein said second solvent is a polar aprotic solvent.
10. The process of embodiment 8 or 9, wherein said polar aprotic solvent has a boiling point of about 40° C. to about 200° C. at 1 atmosphere.
11. The process of any one of embodiments 8-10, wherein said polar aprotic solvent has 0-10% by weight water.
12. The process of any one of embodiments 8-10, wherein said polar aprotic solvent is anhydrous.
13. The process of any one of embodiments 8-12, wherein said polar aprotic solvent has a dielectric constant of 10 to 50 at room temperature and 1 atmosphere.
14. The process of any one of embodiments 8-13, wherein said polar aprotic solvent is acetonitrile, dimethyl sulfoxide (DMSO), dimethylformamide (DMF), dimethylacetamide (DMAC), N-methyl-2-pyrrolidone (NMP), hexamethylphosphoramide (HMPA), N,N'-dimethylpropyleneurea (DMPU), sulfolane, dihydrolevoglucosenone, 1,3-dimethyl-2-imidazolidinone (DMI), or a combination thereof.
15. The process of any one of embodiments 8-14, wherein said polar aprotic solvent comprises dimethyl sulfoxide (DMSO).
16. The process of any one of embodiments 8-15, wherein said admixing is performed in the presence of an acid.
17. The process of embodiment 16, wherein said acid is an alkyl sulfonic acid, an aryl sulfonic acid, an alkyl carboxylic acid or an aryl carboxylic acid.
18. The process of embodiment 16 or 17, wherein said acid is selected from the group consisting of acetic acid, methylsulfonic acid, tolylsulfonic acid, trifluoroacetic acid, trichloroacetic acid, dichloroacetic acid, chloroacetic acid, benzenesulfonic acid, triflic acid, ethylsulfonic acid, formic acid, propionic acid, benzoic acid, salicylic acid, and oxalic acid.
19. The process of any one of embodiments 16-18, wherein said acid comprises acetic acid.
20. The process of any one of embodiments 16-19, wherein said acid is present at 0.01 to 20 volume equivalents based on Compound B or salt thereof.
21. The process of any one of embodiments 16-20, wherein said acid is present at 0.1 to 10 volume equivalents based on Compound B or salt thereof.
22. The process of any one of embodiments 16-21, wherein said acid is present at 0.5 to 3 volume equivalents based on Compound B or salt thereof.
23. The process of embodiment 22, wherein said acid is present at 1 to 2.5 volume equivalents based on Compound B or salt thereof.
24. The process of any one of embodiments 1-23, wherein said admixing is performed in the presence of up to 1.5 molar equivalents of water based on Compound B or salt thereof.
25. The process of any one of embodiments 1-24, wherein said admixing is performed in the absence of water.
26. The process of embodiment 24, wherein the water is present at 0.5 molar equivalents based on Compound B or salt thereof.
27. The process of any one of embodiments 1-26, wherein said admixing is performed at a temperature of 20° C. to 200° C.
28. The process of embodiment 27, wherein said admixing is performed at a temperature of 70° C. to reflux of said solvent.
29. The process of embodiment 27, wherein said admixing is performed at a temperature of 50° C. to 200° C.
30. The process of embodiment 29, wherein said admixing is performed at a temperature of 70° C. to 190° C.
31. The process of embodiment 30, wherein said admixing is performed at a temperature of 130° C. to 135° C.
32. The process of any one of embodiments 1-31, wherein said admixing occurs at a reaction time of 0.1 minute to 48 hrs.
33. The process of any one of embodiments 1-32, wherein said admixing occurs at a reaction time of 4 hr to 36 hours
34. The process of any one of embodiments 1-33, wherein said admixing occurs at a reaction time of 8 to 24 hrs.
35. The process of any one of embodiments 1-34, wherein said admixing occurs at a reaction time of 16 hrs.
36. The process of any one of embodiments 1-31, wherein said admixing occurs at a residence time of 0.1 to 120 minutes.
37. The process of embodiment 36, wherein said admixing occurs at a residence time of 1 minute to 60 minutes.
38. The process of embodiment 37, wherein said admixing occurs at a residence time of 10 minutes to 40 minutes.
39. The process of embodiment 38 wherein said admixing occurs at a residence time of 15 minutes to 30 minutes.
40. The process of embodiment 39, wherein said admixing occurs for a residence time of 25 minutes to 30 minutes
41. The process of any one of embodiments 1-31 and 36-40, wherein said admixing occurs in a plug-flow reactor.
42. The process of any one of embodiments 1-41, wherein said isolating comprises:
   (a) cooling said reaction mixture to a temperature of 0° C. to 50° C. to form a cooled solution;

(b) adding water to said cooled solution; and
(c) precipitating said apremilast from said solution formed in step (b) to isolate said apremilast.

43. The process of embodiment 42, further comprising filtering said precipitated apremilast of step (c).

44. The process of embodiment 42, wherein step (b) further comprises adding crystalline apremilast to said cooled solution such that said precipitating of step (c) results in crystalline apremilast.

45. The process of any one of embodiments 1-41, wherein said isolating comprises continuous crystallization using mixed-suspension, mixed-product removal (MSMPR) crystallizers; parallel filtration, or a combination thereof.

46. A process for isolating apremilast from a reaction mixture comprising crude apremilast and DMSO, comprising:
(a) cooling said reaction mixture to a temperature of 0° C. to 50° C. to form a cooled solution;
(b) adding water to said cooled solution;
(c) precipitating apremilast from said solution formed in step (b) to form precipitated apremilast; and
(d) isolating said precipitated apremilast.

47. The process of embodiment 46, wherein said isolating is by filtering.

48. The process of embodiment 46 or 47, wherein step (b) further comprises adding crystalline apremilast to said cooled solution.

49. The process of any one of embodiments 46-48, wherein said precipitated apremilast is crystalline.

50. A process of preparing apremilast comprising:
(a) admixing (1) a first solution comprising 3-acetamidophthalic anhydride (Compound A) in a first solvent and (2) a second solution comprising (S)-1-(3-ethoxy-4-methoxyphenyl)-2-(methylsulfonyl)ethan-1-amine (Compound B) or a salt thereof in a second solvent to form apremilast in a reaction mixture, wherein the admixing occurs in a continuous process apparatus; and
(b) isolating said apremilast from said reaction mixture, wherein said isolating comprises:
(i) cooling the reaction mixture to a temperature of 0° C. to 50° C.;
(ii) adding water to the cooled reaction mixture;
(iii) precipitating apremilast from the mixture of step (ii); and
(iv) isolating said precipitated apremilast.

51. A process of preparing crystalline apremilast, comprising:
(s) admixing (1) a first solution comprising 3-acetamidophthalic anhydride (Compound A) in a first solvent and (2) a second solution comprising (S)-1-(3-ethoxy-4-methoxyphenyl)-2-(methylsulfonyl)ethan-1-amine (Compound B) or a salt thereof in a second solvent to form apremilast in a reaction mixture, wherein the admixing occurs in a continuous process apparatus; and
(b) isolating crystalline apremilast from said reaction mixture by continuous crystallization and parallel filtration.

52. The process of embodiment 46, wherein said continuous crystallization comprises using mixed-suspension, mixed-product removal (MSMPR) crystallizers.

Embodiments provided herein may be more fully understood by reference to the following examples. These examples are meant to be illustrative of pharmaceutical compositions and dosage forms provided herein, but are not in any way limiting.

EXAMPLES

The following examples further illustrate the disclosed processes, but of course, should not be construed as in any way limiting their scope.

Example 1

Provided herein is an example of a continuous reaction process for preparing apremilast and subsequent continuous crystallization of apremilast, as generally depicted in FIG. 1. 3-Acetamidophthalic anhydride (Compound A, 1.059 kg, 0.99 equiv.) was dissolved in DMSO (14.23 L, 10 L/Kg) in a first feed tank. (S)-1-(3-Ethoxy-4 methoxyphenyl)-2-(methylsulfonyl)ethan-1-amine (Compound B, 1.425 kg, 1.0 equiv) was dissolved in DMSO (1.43 L, 1.0 L/kg) in a second feed tank, and acetic acid (3.56 L, 2.5 L/kg) was added to the solution in the second feed tank. The contents of the first and second feed tanks were pumped into a plug flow reactor at a rate of 9.96 mL/min and 4.0 mL/min respectively. The reaction stream was mixed and heated at 130° C. for a mean residence time ($\tau$) of 25 minutes to form crude apremilast. In order to isolate apremilast, the reaction stream was passed sequentially through a series of three MSMPR vessels. In the first of the three MSMPR vessels, water and the reaction stream were simultaneously added to a seed bed comprising DMSO, water, and crystalline apremilast seed to achieve a mixture containing 30% water, and the temperature of the reaction stream was maintained at 25° C. while being agitated. The resulting slurry was subsequently pumped to the second MSMPR vessel, and water was added to achieve a mixture containing 40% water. The slurry was further transferred to the third MSMPR for additional ageing. The mean residence time in each of the three MSMPRs was 60 minutes. The combined apremilast product was washed with water and ethanol and dried. In the continuous reaction process, the reactants were simultaneously charged and the products discharged from the process system.

In an alternate process for Example 1, the continuous reaction process comprises a number of discrete residence times wherein the material properties of the system reach a steady state and remain constant with time, such that the process is uniform in product output.

Example 2

In another example of a continuous reaction process for preparing apremilast and subsequent continuous crystallization of apremilast, Compound A (222.9 g/0.99 equiv.) was dissolved in DMSO (3.0 L, 10 L/kg Compound B) in a first feed tank, and Compound B (300 g, 1.00 equiv.) was dissolved in DMSO (0.3 L, 1 L/kg) in a second feed tank, acetic acid (0.75 L, 2.5 L/kg) and water (10.2 mL, 0.034 L/kg) were added to the second feed tank. The contents of the first and second feed tanks were pumped into a plug flow reactor, wherein the reaction stream was axially mixed and heated at 130° C. for a mean residence time (–) of 25 minutes in order to form crude apremilast. The crude reaction stream was collected and stored. Apremilast was then isolated from the stored reactant stream. A first volume of the stored reaction stream was crystallized using MSMPRs as described above, and the second volume was crystalized by batch crystallization, wherein water (antisolvent) was added directly to the stored reaction stream and the apremilast precipitate was subsequently filtered, washed and dried. Apremilast was produced in a yield of 98%.

Example 3

Figure 2:
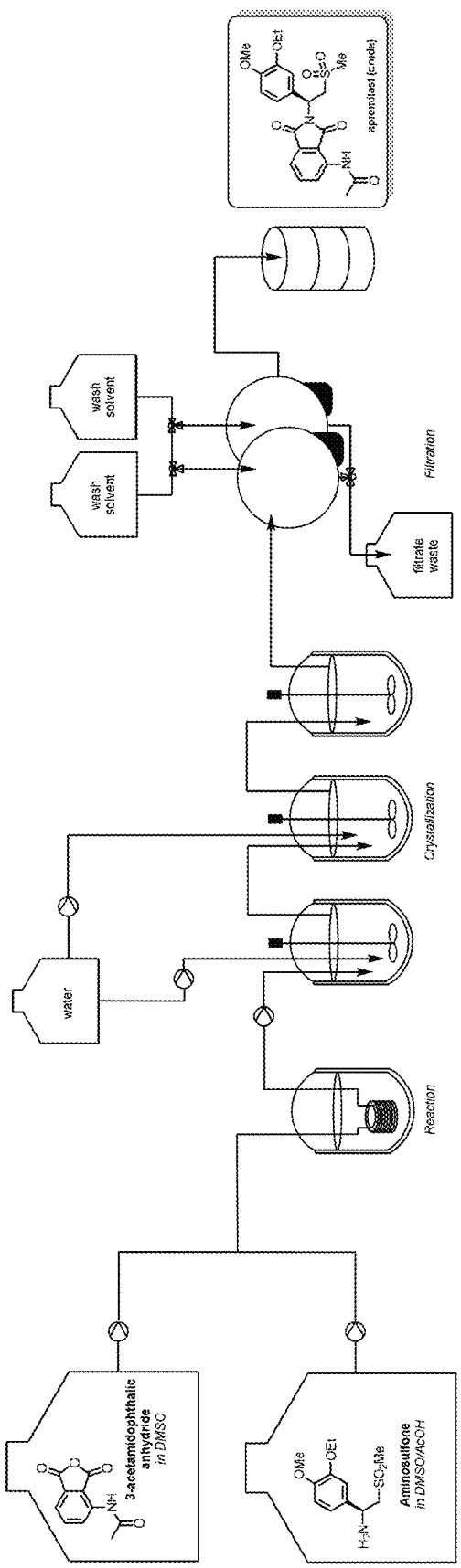
FIG. 2. depicts a process flow diagram for a continuous reaction process and manufacture of apremilast as disclosed herein.

A continuous reaction process and batch crystallization process were employed to prepare apremilast with batch crystallization, as outlined in FIG. 2. Compound A (440 g, 0.99 equiv.) was dissolved in DMSO (6 L, 10 L/kg Compound B) in a first feed tank, and Compound B (594 g, 1 equiv.) was dissolved in DMSO (0.6 L, 1 L/kg) in a second feed tank, acetic acid (1.5 L, 2.5 L/kg) and water (0.2 L, 0.034 L/kg) were added to the second feed tank. The contents of the first and second feed tanks were pumped into a plug flow reactor, wherein the reaction stream was axially mixed and heated at 130° C. for a mean residence time (–) of 20 minutes in order to form crude apremilast. The crude reaction stream was collected and apremilast was then isolated from reactant stream, such that apremilast was produced at a rate of 43 g/hr, the apremilast was crystalized by batch crystallization, wherein water (antisolvent) was added directly to the stored reaction stream and the apremilast precipitate was subsequently filtered, washed and dried.

Example 4

Further experiments were performed for continuous process production of apremilast at various temperatures, flow rates, volumes and residence times. A solution of Compound A (0.99 equiv., 0.35 mol/L) and a solution of Compound B (1.0 equiv, 0.88 mol/L) having a flow rate of 1.57 mmol/min and 1.58 mmol/min respectively, were reacted in a PFR comprising a volume of 125.61 mL, and a residence time of 20 minutes, wherein the reaction stream was heated at a temperature of 130° C., which resulted in apremilast being produced at about 43.33 g/hr, and a daily throughput of about 1.04 kg/24 hr.

Example 5

A solution of Compound A (0.99 equiv., 0.35 mol/L) and a solution of Compound B (1.0 equiv., 0.88 mol/L) having a flow rate of 1.31 mmol/min and 1.32 mmol/min respectively, were reacted in a PFR comprising a volume of 130.84 mL, and a residence time of 25 minutes, wherein the reaction stream was heated at a temperature of 130° C., which resulted in apremilast being produced at about 36.11 g/hr, and a daily throughput of about 0.87 kg/24 hr.

Example 6

Apremilast was produced by a batch process (wherein all reaction materials are charged before the start of processing and discharged at the end of processing), and DMF was used as the polar aprotic solvent. A 100 mL EasyMax reactor was charged with Compound B (5.0 g, 1.0 equiv.); water (0.17 mL, 0.034 mL/g); and a clear solution was obtained on addition of DMF (30 mL, 6 mL/g) to the reactor. The temperature was set to 20° C. and acetic acid (13 mL, 2.5 mL/g) was added slowly by syringe. Compound A (3.8 g, 0.99 equiv.) was then added to the reactor and the reaction mixture heated to 70° C., the reaction was monitored by UPLC and reached completion at a reaction time of 18 hrs. Crude apremilast was produced in a yield of 75%.

Example 7

Apremilast was produced by a batch process, wherein DMSO was used as the polar aprotic solvent. A 100 mL EasyMax reactor was equipped with temperature probe, reflux condenser, nitrogen inlet, and an EasySampler probe; and was charged sequentially with Compound B (6.02 g, 1 equiv.); anhydrous DMSO (36 mL, 6 mL/g); and water (0.20 mL, 0.034 mL/g). A clear solution was obtained upon addition of DMSO (resulting in the full dissolution of Compound B). The reaction mixture was cooled to a temperature of 20° C., then acetic acid (15 mL, 2.5 mL/g) was added slowly via syringe. Solid Compound A (4.48 g, 0.99 equiv.) was added, and the temperature ramped up to 70° C. over 1 hour, and the reaction was then cooled to 35° C. The reaction ran to completion after 10 h.

Example 8

Apremilast can be made via batch crystallization. To a reaction mixture comprising crude apremilast (which may be the product of a batch or a continuous production process) water (6.00 mL, 1.0 mL/g) was added dropwise via syringe pump over 15 minutes at 35° C. and stirred for 20 min at 35° C. 50 mg of apremilast seed (0.5 wt %) was added to the solution. The solution was observed to immediately became cloudy. The slurry was aged at 35° C. for 1 hour, then 3 vol. of water (18 mL, 3.0 mL/g) were added over 1 hour via syringe pump. The cloudy solution was cooled to a temperature of 15° C. over 90 minutes, then stirred at 15° C. overnight. The slurry was filtered, washed with water (25 mL), and dried under nitrogen sweep overnight. Crystalline apremilast (9.47 g) was obtained (99.57% by qnmr; 99.86 LCAP purity), on which $^1$H NMR was performed (1 h nmr (500 mhz, $CD_3SOCD_3$, 300 k) δ (ppm)=9.69 (s, 1 h), 8.46 (d, j=8.3 hz, 1 h), 8.02-7.97 (m, 2 h), 7.77 (dd, j=7.4, 8.3 hz, 1 h), 7.68-7.63 (m, 1 h), 7.58-7.50 (m, 2 h), 7.50-7.44 (m, 2 h), 7.43-7.32 (m, 3 h), 7.09 (d, j=2.2 hz, 1 h), 7.00 (dd, j=2.0, 8.5 hz, 1 h), 6.94 (d, j=8.4 hz, 1 h), 5.80 (dd, j=4.3, 10.5 hz, 1 h), 5.36 (s, 2 h), 4.37 (dd, j=10.6, 14.3 hz, 1 h), 4.16 (dd, j=4.3, 14.3 hz, 1 h), 4.02 (q, j=7.0 hz, 1 h), 3.74 (s, 1 h), 3.32 (s, 1 h), 3.03 (s, 1 h), 2.19 (s, 1 h), 1.32 (t, j=6.9 hz, 1 h).

Example 9

Comparative example (THF batch synthesis): A 100 mL EasyMax reactor was equipped with temperature probe, reflux condenser, nitrogen inlet, and an EasySampler probe; and was charged sequentially with Compound B (6.00 g, 1.0 equiv.), THF (36 mL, 6.0 mL/g), and water (0.20 mL, 0.034 mL/g). The reaction mixture was cooled to a temperature of 15° C., then acetic acid (15 mL, 2.5 mL/g) was added slowly over 2 minutes via syringe, maintaining the internal reaction temperature no greater than 25° C. The temperature was increased to 72° C., and Compound A (4.6 g, 0.99 equiv) was charged as a solid. The reaction was held at 72° C. for 21 hours, then cooled to 30° C. and diluted with isopropyl acetate (51 mL, 8.5 mL/g). A 10% sodium phosphate monobasic solution (30 mL, 5.0 mL/g) was then added over 30 minutes via syringe pump, then stirred for an additional 30 minutes. The mixture was transferred to a separatory funnel and the aqueous layer was removed. The organic layer was washed an additional 2 times with 10% sodium phosphate monobasic solution (30 mL, 5.0 mL/g), then with water (30 mL, 5.0 mL/g) at 30° C. Isopropyl acetate (48 mL, 8.0 mL/g) was added, and the solvent was removed via rotary evaporation. The residue was concentrated again from isopropyl acetate (48 mL, 8.0 mL/g) and the residue was taken up in isopropyl acetate (39 mL, 6.5 mL/g) in a clean 100 mL EasyMax reactor. The solution was heated to 35° C., and methyl t-buyl ether (MTBE) (9.0 mL, 1.5 mL/g) was added; the mixture was stirred for 45 minutes until a cloudy solution was obtained. MTBE (48 mL, 8.0 mL/g) was added over a period of 2 hours via syringe pump. Following the addition, the slurry was cooled to 15° C. over 80 minutes and held at 15° C. overnight. The resulting slurry was filtered, washing with MTBE (18.0 mL, 3.0 mL/g) and dried to provide crystalline apremilast (8.63 g, 97.2 wt % by qNMR, 84% yield).

While examples of certain particular embodiments are provided herein, it will be apparent to those skilled in the art that various changes and modifications may be made. Such modifications are also intended to fall within the scope of the appended claims.

What is claimed is:

1. A process of preparing apremilast comprising:
   admixing in a continuous reaction process (1) a first solution comprising 3-acetamidophthalic anhydride (Compound A) or a salt thereof in a first solvent and (2) a second solution comprising(S)-1-(3-ethoxy-4-methoxyphenyl)-2-(methylsulfonyl)ethan-1-amine (Compound B) or a salt thereof in a second solvent to form a reaction stream comprising apremilast, wherein the admixing occurs at a residence time of 0.1 to 120 minutes; and
   adding water to the reaction stream to isolate the apremilast.

2. The process of claim 1, wherein Compound A or salt thereof is present at 0.4 to 1.5 molar equivalents based on Compound B or salt thereof.

3. The process of claim 1, wherein Compound A in not in salt form.

4. The process of claim 1, wherein said first solvent and said second solvent are the same solvent.

5. The process of claim 1, wherein said first solvent and said second solvent are different solvents.

6. The process of claim 1, wherein said first solvent is a polar aprotic solvent.

7. The process of claim 1, wherein said second solvent is a polar aprotic solvent.

8. The process of claim 6, wherein said polar aprotic solvent has a boiling point of about 40° C. to about 200° C. at 1 atmosphere.

9. The process of claim 6, wherein said polar aprotic solvent has 0-10% by weight water.

10. The process of claim 6, wherein said polar aprotic solvent is anhydrous.

11. The process of claim 6, wherein said polar aprotic solvent has a dielectric constant of 10 to 50 at room temperature and 1 atmosphere.

12. The process of claim 6, wherein said polar aprotic solvent is acetonitrile, dimethyl sulfoxide (DMSO), dimethylformamide (DMF), dimethylacetamide (DMAC), N-methyl-2-pyrrolidone (NMP), hexamethylphoramide (HMPA), N,N'-dimethylpropyleneurea (DMPU), sulfolane, dihydrolevoglucosenone, 1,3-dimethyl-2-imidazolidinone (DMI), or a combination thereof.

13. The process of claim 6, wherein said polar aprotic solvent comprises dimethyl sulfoxide (DMSO).

14. The process of claim 6, wherein said admixing is performed in the presence of an acid.

15. The process of claim 14, wherein said acid is an alkyl sulfonic acid, an aryl sulfonic acid, an alkyl carboxylic acid or an aryl carboxylic acid.

16. The process of claim 14, wherein said acid is selected from the group consisting of acetic acid, methylsulfonic acid, tolylsulfonic acid, trifluoroacetic acid, trichloroacetic acid, dichloroacetic acid, chloroacetic acid, benzenesulfonic acid, triflic acid, ethylsulfonic acid, formic acid, propionic acid, benzoic acid, salicylic acid, and oxalic acid.

17. The process of claim 14, wherein said acid comprises acetic acid.

18. The process of claim 14, wherein said acid is present at 0.01 to 20 volume equivalents based on Compound B or salt thereof.

19. The process of claim 1, wherein said admixing is performed in the presence of up to 1.5 molar equivalents of water based on Compound B or salt thereof.

20. The process of claim 1, wherein said admixing is performed in the absence of water.

21. The process of claim 19, wherein the water is present at 0.5 molar equivalents based on Compound B or salt thereof.

22. The process of claim 1, wherein said admixing is performed at a temperature of 20° C. to 200° C.

23. The process of claim 22, wherein said admixing is performed at a temperature of 70° C. to reflux temperature of the reaction mixture.

24. The process of claim 1, wherein said admixing occurs at a reaction time of 0.1 minute to 48 hrs.

25. The process of claim 1, wherein said admixing occurs in a plug-flow reactor.

26. The process of claim 1, wherein said isolating comprises:
   a. cooling said reaction mixture to a temperature of 0° C. to 50° C. to form a cooled solution;
   b. adding water to said cooled solution; and
   c. precipitating said apremilast from said solution formed in step (b) to isolate said apremilast.

27. The process of claim 26, further comprising filtering said precipitated apremilast of step (c).

28. The process of claim 26, wherein step (b) further comprises adding crystalline apremilast to said cooled solution such that said precipitating of step (c) results in crystalline apremilast.

29. The process of claim 1, wherein said isolating comprises continuous crystallization using mixed-suspension, mixed-product removal (MSMPR) crystallizers; parallel filtration, or a combination thereof.

30. The process of claim 1, wherein the continuous reaction process is conducted on a reaction scale to provide apremilast at a daily throughput of at least about 0.8 kg/24 hours.

31. The process of claim 30, wherein the daily throughput is at least about 1 kg/24 hours.

* * * * *